United States Patent [19]
Osther et al.

[11] Patent Number: 5,830,476
[45] Date of Patent: Nov. 3, 1998

[54] ACTIVE INDUCTION OR PASSIVE IMMUNIZATION OF ANTI-GP48 ANTIBODIES AND ISOLATED GP48 PROTEIN

[75] Inventors: Kurt B. Osther, Hopkinton; Chung-Ho Hung, Milford, both of Mass.

[73] Assignee: Verigen, Inc.

[21] Appl. No.: 306,605

[22] Filed: Sep. 15, 1994

Related U.S. Application Data

[60] Continuation-in-part of Ser. No. 195,617, Feb. 14, 1994, Pat. No. 5,516,895, which is a division of Ser. No. 772,604, Oct. 8, 1991, Pat. No. 5,286,852.

[51] Int. Cl.$^6$ .......................... A61K 39/21; A61K 39/00; A61K 39/42; A01N 63/00
[52] U.S. Cl. ..................... 424/208.1; 424/184.1; 424/93.1; 424/160.1; 435/72.1
[58] Field of Search ................ 424/184.1, 93.1, 424/208.1, 160.1; 435/72.1

[56] References Cited

U.S. PATENT DOCUMENTS 5,286,852  2/1994  Osther et al. ...................... 530/388.35

OTHER PUBLICATIONS

Buchegger et al., (1987) Swine Monoclonal Antibodies of High Affinity and Specificity to Carcinoembryonic Antigen, JNCI 79(2):337–342.

Osther et al., (1992) PASSHIV-1 treatment of patients with HIV-1 infection. A preliminary report of a Phase I trial of hyperimmune porcine immunoglobulin to HIV-1, AIDS 6:1457–1464.

Kwang et al. Vetrinary Microbiology 32(3–4) pp.281–92. Oct. 1992.

*Primary Examiner*—Donald E. Adams
*Assistant Examiner*—Brett L. Nelson
*Attorney, Agent, or Firm*—McDonnell Boehnen Hulbert & Berghoff

[57] ABSTRACT

The instant invention provides for isolated gp48 glycoprotein, methods of passive immunization with anti-gp48 antibodies, and methods of active immunization for generating anti-gp48 antibodies.

4 Claims, 4 Drawing Sheets

ACTIVE INDUCTION OR PASSIVE IMMUNIZATION OF ANTI-GP48 ANTIBODIES AND ISOLATED GP48 PROTEIN

This application is a Continuation-in-Part application of U.S. Ser. No. 08/195,617 filed Feb. 14, 1994 (now U.S. Pat. No. 5,516,895 issued May 14, 1996) which was a Divisional of U.S. Ser. No. 08/772,604 filed Oct. 8, 1991 (now U.S. Pat. No. 5,286,852 issued Feb. 15, 1994).

BACKGROUND OF THE INVENTION

In U.S. Pat. No. 5,286,852 (hereby incorporated in full by reference) it was shown that pigs immunized with certain HIV-1 lysate isolates (HIV-1 lysate from Cellular Products, Inc., Buffalo, Advanced Biotechnologies Inc., Colombia, Md.) produced antibodies that, have specificity to a glycoprotein which, on HIV-1 Western blots (e.g., HIV-1 Western blots from Organon Teknika, produced by Epitope, U.S.), appears in the region ranging from 46,000 Daltons to 53,000 Daltons. This band appears as a broad band and was named gp48.

Pigs immunized with recombinant HIV-1 proteins, such as gag(rgp24), and env (rgp160, rgp120, Agmed) don't produce antibodies reactive to gp48. As described in the '852 patent, the precise origin of this protein, present in the HIV-1 lysate, was not established but was thought to be either related to HIV-1 proteins or to cell membrane proteins from human cells that are CD4 positive (CD4+).

The in vivo effect of anti-gp48 porcine immunesera (formulated as PASSHIV-1™) on HIV-1 infected humans, and in humans suffering from AIDS, has been described by Osther et al. (Osther, K. et al., *AIDS* 1992, 6, 1457 hereby incorporated by reference). Some of the patients receiving PASSHIV-1 had normal CD4 counts and would be considered immunocompetent. To date, approximately twenty to thirty patients have been infused i.v. with PASSHIV-1 consisting of at least one cycle with 0.3 to 15 grams daily for a period of five days. It definitely appears that the presence of anti-gp48 in antibody preparations used for passive treatment of HIV-1 infected and AIDS patients, is important in the protection from expansion of infection.

SUMMARY OF THE INVENTION

The instant invention provides for isolated gp48 protein, which is identified by immunoreactivity with anti-gp48 antisera. The isolated gp48 is useful as a specific marker or standard protien for the isolation of related gp48 proteins from other sources, and for the identification of such proteins during assay procedures. For example in testing clinical sample isolates, culture isolates, tissue isolates and other samples to be tested for the presence of gp48 protein. The gp48 protein can be isolated from CD4+ cells, viral lysates, H9 cells, tissues and organs. In a preferred embodiment, the gp48 is isolated from H9 cells.

The instant invention also provides for methods of generating an anti-gp48 antibody in a mammal by active immunization comprising, immunizing the mammal with an effective amount of gp48 protein. In one embodiment the gp48 protein is substantially purified. In other embodiments the gp48 protein is a component of a cell lysate, is a component of a viral lysate, is a component of a protein mixture, or is produced from recombinant DNA.

The instant invention further provides for methods of passive immunization of a mammal comprising, immunization with an effective amount of anti-gp48 antibodies. In a preferred embodiment the anti-gp48 antibodies are of porcine origin. In other embodiments, the anti-gp48 antibodies are polyclonal or monoclonal, are administered in combination with HIV-1 virus, are introduced together with any heterologous protein or tissue.

The instant invention also provides a method of actively or passively reducing the immunogenicity of a protein comprising, immunizing a mammal with a protein in combination with anti-gp48 antibodies.

DETAILED DESCRIPTION OF THE INVENTION

Figure 1:
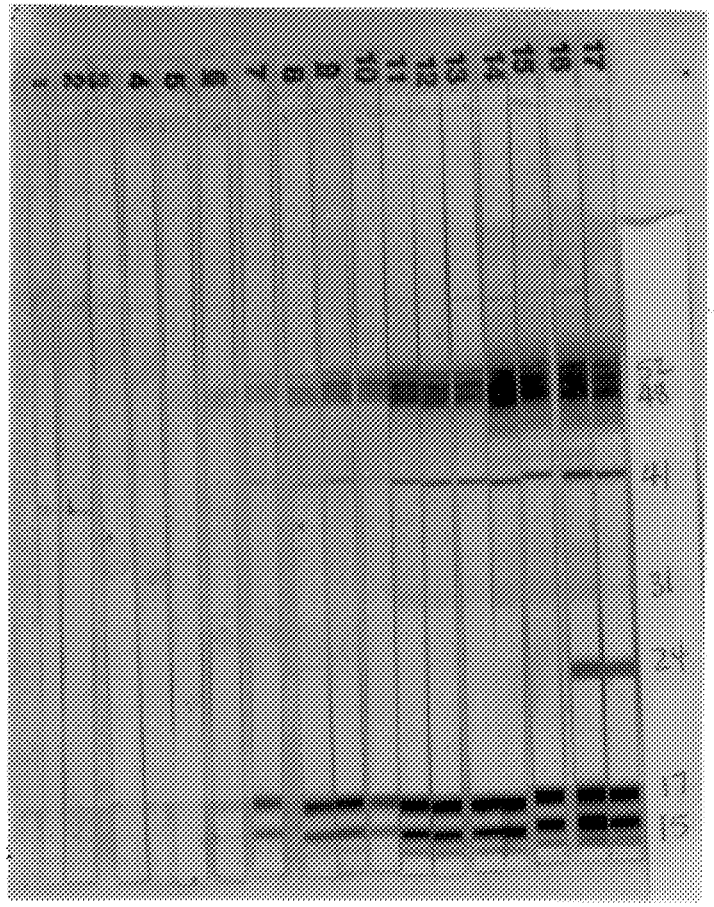
FIG. 1 is a series of HIV-1 Western Blot Strips (1–17) showing the seroconversion to anti-gp48 positive serum. The gp48 protein is isolated to the region marked 48–52.
Figure 2:
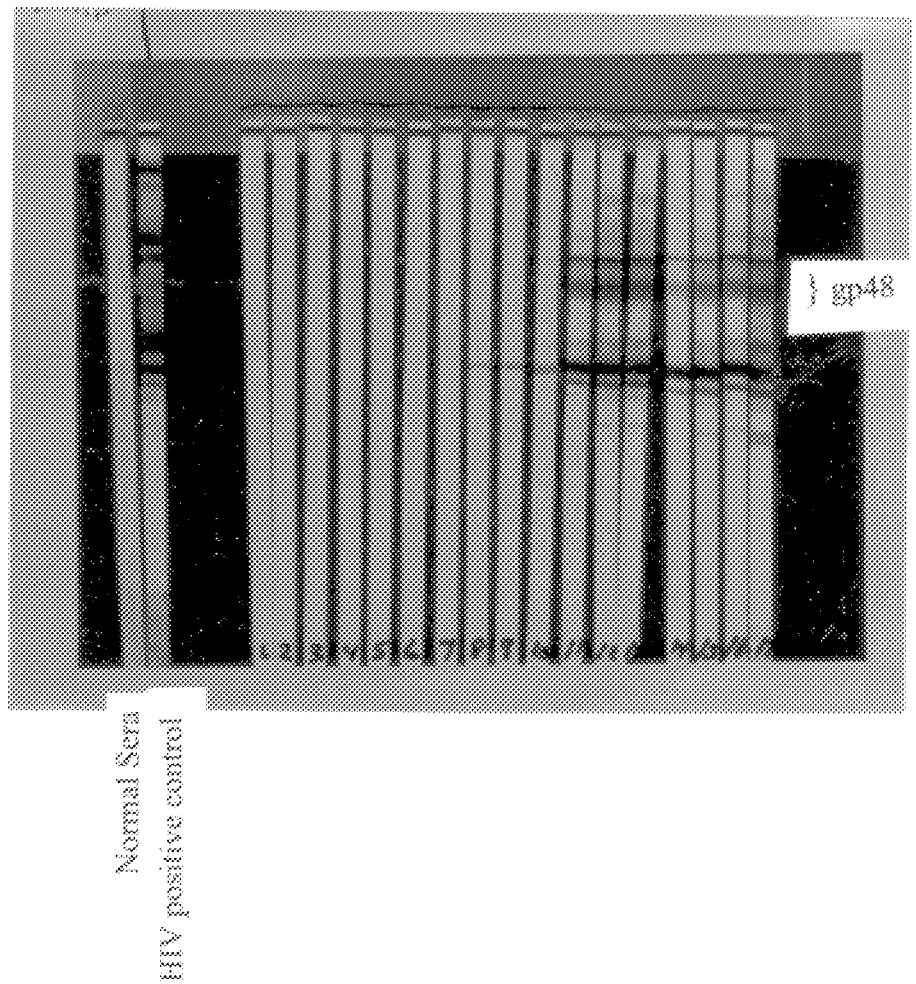
FIG. 2 is a series of HIV-2 Western Blot Strips (1–17), negative control strip (N), and positive HIV-2 strip (P) showing the seroconversion to anti-gp48 positive serum. The gp48 protein is isolated to the region marked 48.

When porcine antibodies against HIV-1 lysates (containing gp48) was administered (up to 14 grams of porcine immunoglobulin G daily during a five day period) to the above-described HIV-1 infected or AIDS patients, HIV-1 Western blots done on serum samples from the patients prior to, during, and post i.v. infusion with would sometimes show an increase in anti-HIV-1 antibodies on Western blots. Suprisingly, there was usually never any detectable anti-gp48 antibodies in patient's sera, even after infusion of substantial (up to 14 grams) amounts of porcine IgG anti-gp48, only the normal antibodies to the other proteins common to the HIV-1 lysates. Surprisingly in the human patients, independent of their HIV-1 infection stage (ranging from asymptomatic infections to full-blown AIDS), the anti gp48 was being adsorbed or bound under this immunization schedule, indicating that gp48 was present in the patients. Certain Patients were able to eventually seroconvert to production of anti-gp48.

The Examples illustrate the determination of the source of gp48 protein, and the characterization of the protien. It was shown that anti-gp48 antibodies could be generated by the immunization of HIV-1 viral lysates ('852 patent), but suprisingly it is shown that the same response is generated by the immunization with HIV-2 viral lysate and H9 cells. Control experiments showed that anti-gp48 was not generated by immunization with HIV proteins. It was shown that gp48 is a membrane surface protein found on CD4+ cells.

Thus anti-gp48 and HIV-1 may compete for access to an area on the cell membrane, including the gp48 membrane protein location. Thereby, the content of anti-gp48 in preparations used in passive immunotherapy of HIV-1 infected individuals may actively participate in preventing subsequent HIV-1 infection of uninfected CD4+ cells.

There is in vivo evidence that anti-gp48 correlates with the absence of symptoms of classical AIDS in HIV infected patients. Thus patients with anti-gp48 antibody already present may even be protected against HIV-1 infection, or may limit the expansion of an HIV-1 infection.

At least one of the patients tested clincally, was anti-gp48 positive on HIV-1 Western blot, and did show evidence of HIV-1 infection by PCR. This patient seroconverted to be anti gp48 positive when tested on HIV-1 Western blots in 1986. Even though to date, the patient has not shown any evidence of a classical HIV-1 infection as defined by identifiable antibodies against classical HIV-1 proteins, and has remained anti-gp48 positive. This is even more suprising given that this patient was subjected to a kidney transplantation in 1987, and would be expected to have developed HIV-1 related symptoms due to the fact that this type of patient receive immunosuppressive drugs in order to prevent kidney rejection. Thus the presence of anti gp48 antibodies in patients may protect them at least against developing HIV-1 infections. Therefore the protein and methods of the instant invention provide for an alternative vaccination approach against HIV-1 infections, against HIV-2 infections, amd any other retrovirus infection that encompasses binding to CD4+ cells. The instant invention provides for a vaccine which would not be dependent upon structural mutations in a virus, such as for instance HIV-1 strains.

Thus the instant invention provides for an isoltated gp48 protein which is identified by reactivity with anti-gp48 antisera. The instant invention provides for useful compositions for the detection of related gp48 protein during purification of proteins. The gp48 protein is useful as a size marker and protein standard. The gp48 protein is useful for the detection of specific anti-gp48 antibodies in the sera or tissue samples. The isolated gp48 protein is useful for the active immunization of subjects for the generation of an anti-gp48 immune response in the subject.

Further the instant invention provides for methods of active or passive immunization of subjects for the generation of anti-gp48 antibodies in the subject. The methods of the instant invention are thus useful for the generation of a specific immune response to gp48 and the production of antibodies thereto. The methods of the instant invention provide useful methods for obtaining a specific immune response to gp48.

Using Ouchterlony immunodiffusion, it was not possible to detect any human antibodies to porcine immunoglobulins (HAPA), in the patients. Some of the sera were tested with a porcine IgG Western blot and also showed no human anti-porcine antibodies (HAPA). Thus immunization of foreign protein with anti-gp48 proteins may modify the immunogenicity of the foreign protein. Thus the instant invention also provides for the reduction of the immunogenicity of a protein by immunization in combination with anti-gp48 antibodies.

The following exampes are meant by way of illustration, and are not intended to limit the disclosure of the instant invention.

EXAMPLE 1

Anti-gp48 from HIV-1 lysates

In order to demonstrate seroconversion in pigs immunized with inactivated HIV-1 lysate, one pig was immunized with inactivated HIV-1 lysate (HTLV-IIIB, Organon Teknika) having a protein concentration of 0.90 mg/ml, at a dose of 100 μg per vaccination. The first vaccination consisted of HIV-1 lysate emulsified in Freund's Complete Adjuvant and was administered subcutaneously. The second immunization consisted of HIV-1 emulsified in Freund's Incomplete Adjuvant and was administered subcutaneously on day 2, the third immunization was given day 17, the fourth immunization was given day 31.

The first appearance of anti-gp48 antibodies on HIV-1 Western blot strips (from Pan Data Systems Inc.) was observed on strip No. 6 (FIG. 1, photo of HIV-1 Blot) together with HIV-1 specific protein bands. Strip No. 6 was reacted with serum sample from blood drawn on day 11. The gp48 protein appears to be highly immunogenic in pigs. And under proper conditions, illicit the same immune response in any subject.

EXAMPLE 2

Anti-gp48 from HIV-2 Lysates

Suprisingly, It was found that when immunizing pigs with HIV-2 lysate derived from CD4+ cells, such as H9 cells, a reaction to gp48 was found, as shown by an HIV-2 Western blot and the same as on an HIV-1 Western Blot. (HIV-2 Western blot, Genetic Systems, Seattle, Wash.; FIG. 2).

In order to study the seroconversion in pigs immunized with inactivated HIV-2 lysate, one pig was immunized with inactivated HIV-2 lysate (Hillcrest Biologics Inc.) having a protein concentration of 0.86 mg/ml, at a dose of 100 μg per vaccination. The first vaccination consisted of HIV-2 lysate mixed with Freund's Complete Adjuvant and was administered subcutaneously. The second immunization consisted of HIV-2 mixed in Freund's Incomplete Adjuvant and was administered subcutaneously on day 2, the third immunization was given day 17, the fourth immunization was given day 31. The first appearance of anti gp48 antibodies on HIV-2 Western blot strips (from Genetic Systems Inc.) was observed on strip No. 11 (FIG. 2) together with HIV-2 specific protein bands. Strip No. 11 was reacted with serum sample from blood drawn on day 23. These results show that the anti-gp48 response can be generated by the immunization of HIV-2 as detected by HIV lysates.

EXAMPLE 3

Anti-gp48 from H9 Cells

Suprisingly, It was found that when immunizing pigs with lysed H9 cells alone, it also appeared that anti-gp48 antibodies were produced.

One pig (mixed Yorkshire) was immunized with non-infected H9 cell lysate supernatant from Gottfried Kellermann's Farm, Osceola in December of 1987. The protein concentration of the supernatant was not measured. The pig was immunized with 1 ml of the supernatant emulgated with 1 ml of Freund's Complete Adjuvant. Booster doses was mixed in Freund's Incomplete Adjuvant and given subcutaneously on the neck of the pig every second to third week. After one to two boosters, blood withdrawn from an ear vein of the pig was tested on HIV-1 Western blots (HIV-1 Quick Western blot, Verigen Inc.). A diffuse protein band was detected in the gp48 region indicating that the pig had developed antibodies to a cellular component from H9 (CD4+) cells. Serum from this pig appeared to only contain antibody reaction against gp48 when tested on HIV-1 Western blot strips. This is indicative that gp48 protein is originated from the H9 cell culture, meaning from a CD4+ human cell line, even if the cell is an immortal T cell lymphoblastoid cell line, produces the gp48 protein. It is anticipated that CD4+ cells will have gp48 protein as part of their cell membrane. This immunization trial repeated with H9 cells should show similar results. These results show that the gp48 protein is a component of the cell line used to make the immunization, and that the presence in HIV lysates is a result of the loss from cells and not the HIV.

EXAMPLE 4

Control Experiments

A. It was found that when immunizing pigs with gp120, gp160 and recombinant p24 (rp24) recombinant HIV proteins, into pigs, no anti-gp48 antibodies were developed.

Three Yorkshire mixed bred pigs at Gottfried Kellermann's farm in Osceola were immunized with recombinant gp160 (rgp160), recombinant gp120 (rgp120), and recombinant p24 (rp24), respectively, and one pig (mixed Yorkshire) at East Acre Farm in Massachusetts was immunized with rgp120MN. The pigs were injected subcutaneously with either of these recombinant proteins mixed with Freund's Complete Adjuvant for first vaccination and with Freund's Incomplete Adjuvant for the following vaccinations. When hyperimmune serum from these pigs were tested on HIV-1 Western blots antibodies specific to the recombinant proteins used for the immunizations were present. However, there was no reaction in the said gp48 region. The results show that an anti-gp48 reaction cannot be induced by any of the above recombinant HIV-1 proteins.

B. Blood has been drawn from non-immunized Yorkshire mixed bred pigs and tested on HIV-1 Western blots. No anti-gp48 reaction has been found in any of these pigs, indicating that anti-gp48 is not an antibody already present in non-immunized pigs.

C. Anti-gp48 antiserum samples were tested on HIV-1 recombinant Western blot strips. No reaction was detected on these recombinant Western blot strips indicating that gp48 is not a part of the HIV-1 related epitopes on these types of strips (British Biotech and Chiron).

EXAMPLE 5 gp48 Heat Sensitivity

When comparing human anti-gp48 serum with porcine serum containing anti-gp48 activity, it is apparent on HIV-1 Western blots that the localization as well as the appearance of the reaction proteins on the strips are similar. When gp48 containing protein preparations (such as HIV-1 lysate) are heat inactivated at 60° C.; then transblotted onto nitrocellulose paper; then reacted with anti-gp48 serum from pigs or from humans, the protein reaction is decreased considerably, showing that the gp48 is heat sensitive. When the gp48 containing protein preparation is mixed with 0.1% Sodium Dodecyl Sulphate (SDS) and then heat inactivated at 90° C.; transblotted onto nitrocellulose paper; and reacted with anti-gp48 serum from either humans or from pigs, no gp48 reaction can be observed. The SDS does not protect the gp48 protein.

EXAMPLE 6

Detection of gp48 from H9 Cells: Characterization

A. Uninfected H9 cells are grown in RPMI 1640 medium with 10% fetal bovine serum and harvested by centrifugation. The packed cells are then resuspended in 0.5% NP401 50 mM Tris HCl, pH 6.54 in order to extract soluble proteins. Both the soluble and the insoluble fractions of the cell extract were assayed for the presence of gp48 by Western blot using porcine or human anti-gp48 serum, a gp48 reaction could be detected in blotted proteins from the soluble phase but not from the insoluble fraction.

When uninfected H9 cells were stripped of cell membrane proteins; but would not render the cell lysed, the supernatant would then contain gp48 that when blotted onto Western blot would react with anti-gp48 serum. Thus the gp48 protein is a cell surface protein relatively loosely bound to the cell surface. The gp48 protein found in viral lysate has the same electrophoretic mobility as the gp48 originated from the uninfected H9 cells. Both gp48 originated from viral lysate and from uninfected H9 cells show identical heat sensitivity indicating that these proteins have common physical/chemical characteristics and are essentially the same.

B. Attempts to purify the gp48 proteins on ion exchange columns, showed that gp48 exhibits some characteristics typical of membrane proteins, e.g., tendency to aggregate, improved solubility of the protein in detergents. The content of gp48 in H9 cells is 0.01% or lower of the total cellular proteins as a rough estimate.

C. When a mouse monoclonal anti-HLA class I antibody (DR, DQ, DP) was used for incubation with HIV-1 lysate (gp48 containing) Western blots, a narrow reaction band was found in the lower gp48 region where we previously have found a superimposed protein band. When performing a competitive binding assay with anti-gp48 antiserum and the mouse monoclonal anti-HLA class II antibody, it appeared that the mouse monoclonal antibody does not compete with each other, and are different proteins.

EXAMPLE 7

It was found that uninfected H9 cells when incubated with purified porcine anti-HIV-1 lysate (anti-gp48) immunoglobulin, formulated as PASSHIV-1, (Verigen, San Diego), would bind the anti-gp48 whereas HIV-1 (HTLV-IIIB) infected H9 cells, and uninfected Molt 4 clone 8 cells did not bind anti-gp48.

Briefly, the test consisted of pelleting $5 \times 10^7$ uninfected H9 cells, $5 \times 10^7$ HIV-1 (HTLV-IIIB) infected H9 cells and $5 \times 10^7$ uninfected Molt 4 clone 8 cells, respectively, with 500 ul of PASSHIV-1 for thirty minutes at room temperature, pelleting the cells and either apply the supernatant to HIV-1 lysate Western blots (Organon Teknika). An alternative test consisted of incubating the supernatant from fresh cells of the above-described types as above, and after pelleting, reacting this supernatant with the HIV-1 Western blots.

The Western blots show that uninfected H9 cells removed anti-gp48 to a certain degree by a single incubation, and to a significantly higher degree using repeated incubation with fresh cells. The anti-gp48 was not removed by the experiment involving the HIV-1 (HTLV-IIIB) infected cells and the uninfected Molt4 clone 8 cells, as indicated by results of the HIV-1 Western blots.

Therefore CD4+ uninfected H9 cells have available gp48 cell membrane proteins that can bind anti-gp48, whereas HIV-1 infected H9 cells do not present significant gp48 membrane protein. One of the reasons for the absent reaction with the surface membrane gp48 protein on infected H9 cells, may be that the HIV-1 (via envelope proteins) binds to the region where gp48 membrane protein is present, and thereby preventing anti-gp48 antibody from being bound.

EXAMPLE 8

Purification of gp48

H-9 cells were grown in RPMI 140 supplemented with 10% fetal calf serum, 0.5 mg/ml of glutamine and 0.1 mg/ml of gentamicin and harvested by centrifugation at 600 xg for 10 minutes. After washing once with PBS, the packed cells were resuspended in 10 mM Tris HCL, pH 8.0/0.02 mM $MnCl_2$/0.2% Zwittergent 312 detergent (Calbiochem) to solubilize gp48. Insoluble material was then removed by centrifugation at 10,000 xg for 30 minutes. No gp48 could be found in the pellet.

The supernatant was then loaded onto a lentil lectin sepharose 4B column, equilibrated in 10 mM Tris HCl, pH 8.0 containing 0.02 mM $MnCl_2$, 0.1% Zwittergent 312, and 2 mM DTT. After washing with two column volumes of the equilibration buffer, the column was eluted with 2% methyl-α,D-mannopyranoside. About 50% of the gp48 could be found in the mannuside eluate, whereas the vast majority of the other cellular components was in the flow through. Rechromatography of the flow through did not recover any significant amount of gp48 protein.

This procedure provided a substantial purification of gp48 protein, and suggested that it is a glycoprotein which carries a carbohydrate moiety specific for interaction with lentil lecitin.

Figure 3:
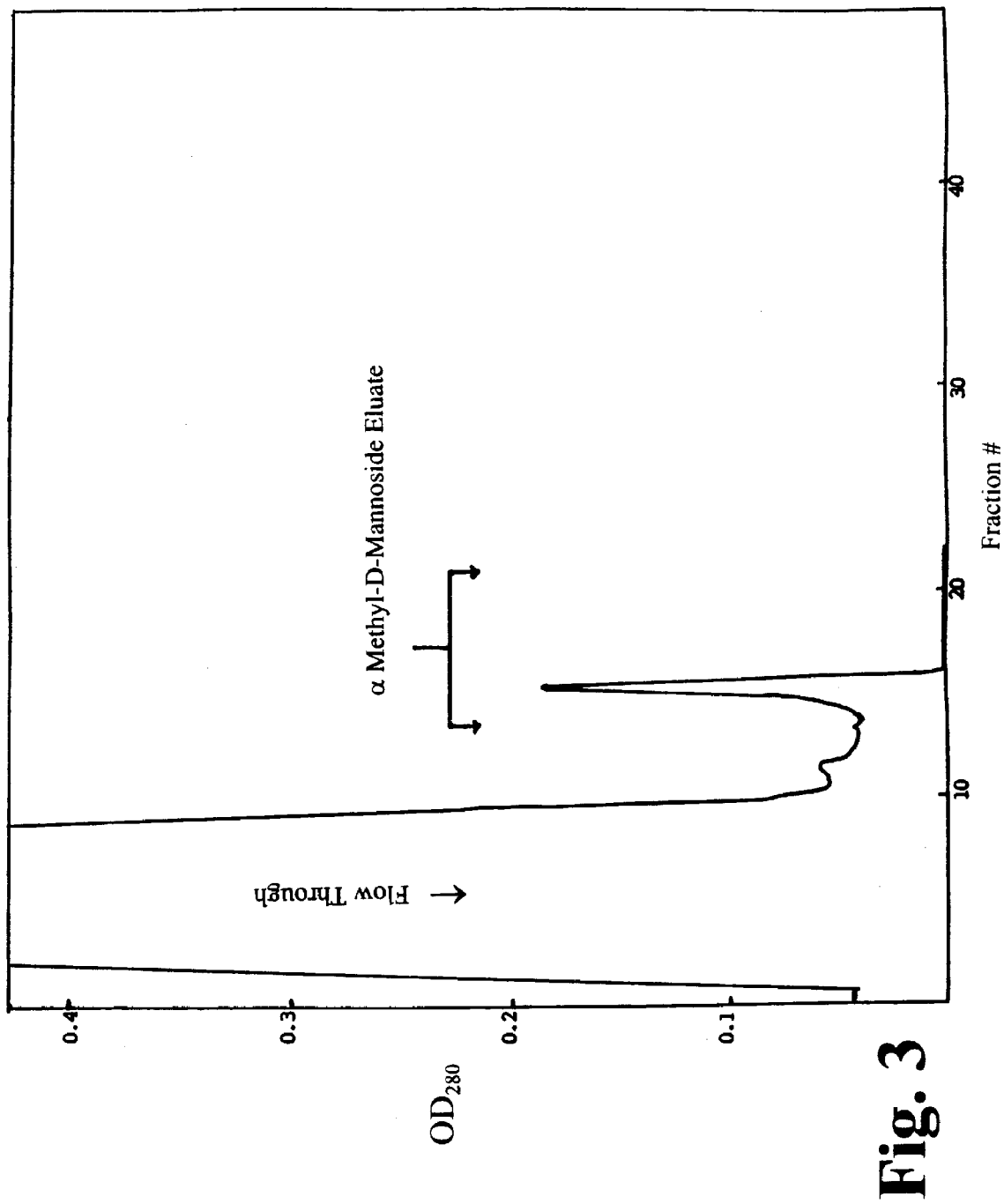
FIG. 3 shows the elution profile of gp48.
Figure 4A:
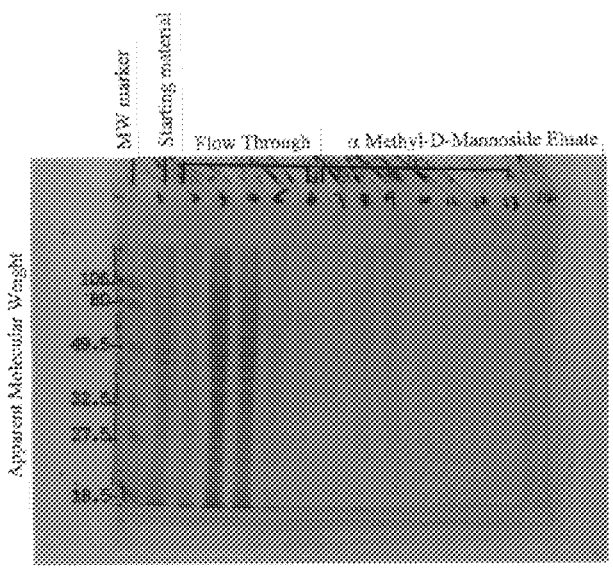
FIG. 4a shows the analysis of the protein from the column by coomassie blue stain and FIG. 4b shows the transferred proteins on a Western blot for gp48.
Figure 4B:
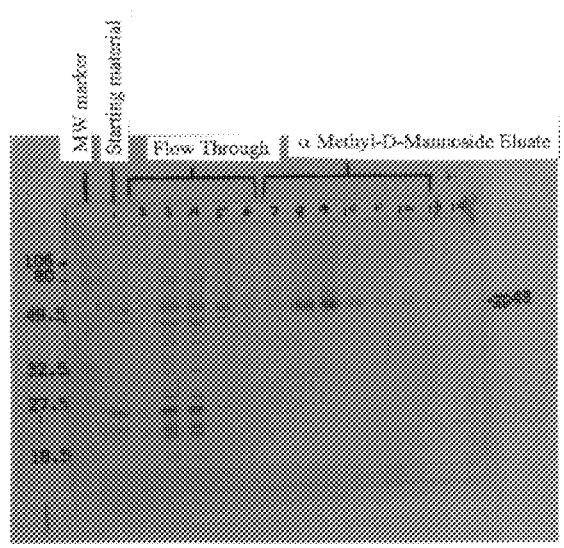

FIG. 3 shows the elution profile from the lentil lecitin column. FIG. 4a shows an SDS page gel stained to show the proteins during purification, and FIG. 4b shows a western blot for gp48 transferred from the protein gel.

Those skilled in the art will know, or be able to ascertain, using no more than routine experimentation, many equivalents to the specific embodiments of the invention described herein.

These and all other equivalents are intended to be encompassed by the following claims.

We claim:

1. A method for generating an anti-gp48 antibody in a mammal by active immunization comprising, immunizing a mammal with an effective immune response eliciting amount of gp48 protein from non-HIV infected $CD4^+$ human cells, HIV viral lysate, or HIV cell lysate, in a suitable carrier.

2. A method of claim 1 wherein the gp48 protein is substantially purified.

3. A method of claim 1 wherein the gp48 protein is a component of H9 cell lysate.

4. A method of claim 1 wherein the gp48 protein is a component of a protein mixture.

* * * * *